(12) United States Patent
Narula et al.

(10) Patent No.: US 7,312,187 B2
(45) Date of Patent: Dec. 25, 2007

(54) POLYALKYLBICYCLIC DERIVATIVES

(75) Inventors: Anubhav P. S. Narula, Hazlet, NJ (US); Edward Mark Arruda, Cliffwood, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 458 days.

(21) Appl. No.: 10/672,339

(22) Filed: Sep. 26, 2003

(65) Prior Publication Data

US 2004/0110991 A1    Jun. 10, 2004

Related U.S. Application Data

(63) Continuation-in-part of application No. 10/635,954, filed on Aug. 7, 2003, now Pat. No. 7,160,852, which is a continuation-in-part of application No. 09/859,953, filed on May 17, 2001, now Pat. No. 6,632,788.

(51) Int. Cl.
*A61K 8/18* (2006.01)
*A61Q 13/00* (2006.01)

(52) U.S. Cl. .............. 512/13; 512/8; 512/14; 512/15; 512/16; 512/17; 512/18; 512/19; 512/22; 512/23; 512/24; 512/25; 512/26; 512/27; 568/376; 568/445

(58) Field of Classification Search .......... 512/8, 512/22, 23, 24, 25, 26, 27, 14, 15, 16, 17, 512/18, 19; 568/376, 445
See application file for complete search history.

(56) References Cited

U.S. PATENT DOCUMENTS

| | | | |
|---|---|---|---|
| 3,767,713 A | 10/1973 | Theimer | |
| 3,847,993 A | 11/1974 | Hall et al. | |
| 3,927,083 A | 12/1975 | Hall et al. | |
| 4,534,891 A | 8/1985 | Boden et al. | |
| 4,902,672 A | 2/1990 | Sprecker et al. | |
| 5,227,367 A | 7/1993 | Boden et al. | |
| 5,665,698 A * | 9/1997 | Narula et al. | 512/19 |
| 5,733,866 A | 3/1998 | Narula et al. | |
| 6,271,193 B1 | 8/2001 | Sprecker et al. | |
| 6,632,788 B2 | 10/2003 | Levorse, Jr. et al. | |

FOREIGN PATENT DOCUMENTS

EP    0 395 199 A1    10/1990
EP    0 825 166 A2    2/1998

* cited by examiner

*Primary Examiner*—Jill Warden
*Assistant Examiner*—Keri A Moss
(74) *Attorney, Agent, or Firm*—Elizabeth M. Quirk; Joseph F. Leightner

(57) ABSTRACT

Described are polyalkylbicylic chemical derivatives for use a fragrance ingredients having the generic structure:

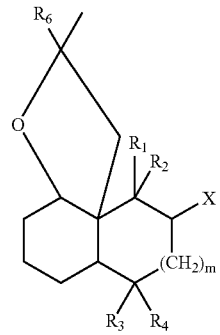

wherein m=0 or 1; wherein X is methyl or hydrogen;
wherein $R_1$, $R_2$, $R_3$ and $R_4$ each represents methyl or ethyl with the proviso that when X is methyl, each of $R_1$, $R_2$, $R_3$ and $R_4$ is methyl and when X is hydrogen, one of $R_1$, $R_2$, $R_3$ and $R_4$ is ethyl; and
wherein $R_6$ represents hydrogen or methyl. Methods for using and making these compounds are also disclosed.

12 Claims, No Drawings

POLYALKYLBICYCLIC DERIVATIVES

RELATED PATENT APPLICATIONS

This application is a continuation-in-part of Application for U.S. patent application Ser. No. 10/635,954 filed on Aug. 7, 2003 now U.S. Pat. No. 7,160,852 which is a continuation-in-part of Application for U.S. patent application Ser. No. 09/859,953 filed on May 17, 2001 now U.S. Pat. No. 6,632,788.

FIELD OF THE INVENTION

The present invention relates to new chemical entities and the incorporation and use of the new chemical entities as fragrance chemicals.

BACKGROUND OF THE INVENTION

Each of U.S. Pat. Nos. 5,227,367; 5,733,866; and 5,665,698 hereby incorporated by reference as set forth in each of their entireties discloses polycyclic chemicals that are suitable for use as fragrance chemicals. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel compounds, represented by the following structure:

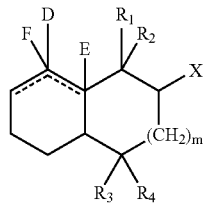

wherein m is 0 or 1;

wherein each of the dashed lines represent a carbon-carbon single bond or a carbon-carbon double bond with the proviso that not more than one dashed line represents a carbon-carbon double bond;

wherein X represents hydrogen or methyl;

wherein $R_1$, $R_2$, $R_3$ and $R_4$ each represent methyl or ethyl with the proviso that when X is methyl, each of $R_1$, $R_2$, $R_3$ and $R_4$ is methyl and when X is hydrogen, one of $R_1$, $R_2$, $R_3$ and $R_4$ is ethyl;

wherein D is =O when neither dashed line is a double bond, —$OR_5$ when either of the dashed lines is a double bond, —$OR_7$ when the dashed line in the Δ4,5 position is a double bond, or

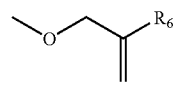

when the dashed line in the Δ3A,4 position represents a double bond;

wherein $R_6$ is hydrogen or methyl;

wherein $R_7$ represents $C_1$-$C_3$ lower alkyl;

wherein $R_5$ represents $C_4$-$C_7$ cycloalkyl, $C_4$-$C_7$ hydroxyalkenyl or tri-$C_1$-$C_3$ lower alkyl silyl;

wherein E is hydrogen or

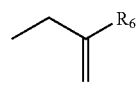

when neither dashed line is a double bond;

wherein F is hydrogen when neither dashed line is a double bond and D is not =O;

wherein D and E taken together represents the moiety:

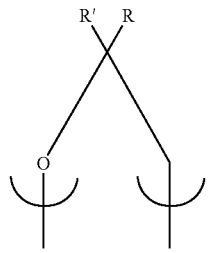

when neither dashed line is a double bond;

wherein R and R' each represents hydrogen or methyl with the proviso that at least one of R and R' is methyl and processes for preparing such compounds.

Another embodiment of the invention is a method for enhancing a fragrance by incorporating an olfactory acceptable amount of one or more of the compounds provided above.

Other embodiments of the invention are processes for preparing the compounds provided above.

These and other embodiments of the present invention will be apparent by reading the following specification.

DETAILED DESCRIPTION OF THE INVENTION

The novel compounds of the present invention are more fully described by the following structures:

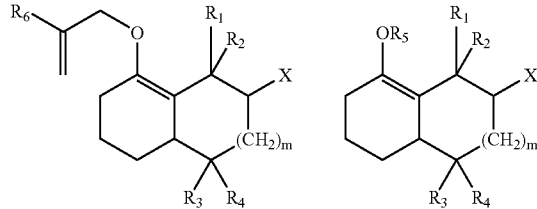

-continued

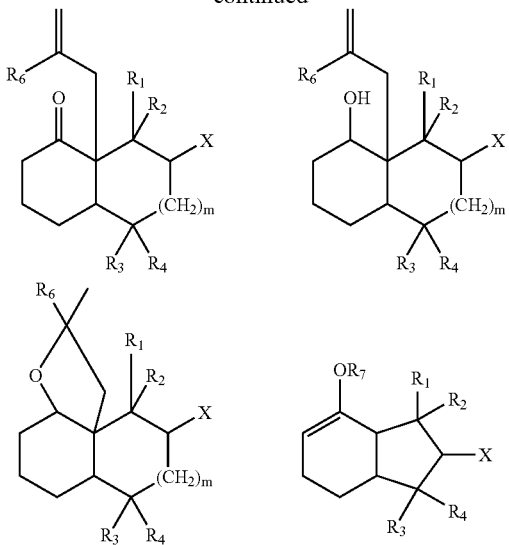

wherein $R_1$, $R_2$, $R_3$, $R_4$, $R_5$, $R_6$, $R_7$, X and m are defined above.

In a preferred embodiment the molecules contain the ring structure wherein $R_6$ is methyl and m=0; and such preferred molecules have the following structures:

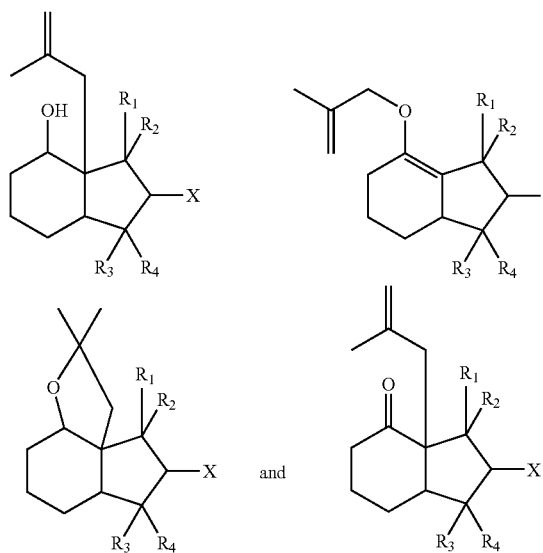

wherein $R_1$, $R_2$, $R_3$, $R_4$, and X are defined above.

In a more preferred embodiment, each of the immediately preceding four structures represents mixtures wherein in each of the mixtures the major molecule (greater than or equal to about 90%) is the one where X represents methyl and each of $R_1$, $R_2$, $R_3$, and $R_4$ represents methyl and the molecules in minor amount (less than or equal to about 10%) are the ones where X is hydrogen and one of $R_1$, $R_2$, $R_3$ and $R_4$ is ethyl and each of the other of $R_1$, $R_2$, $R_3$ and $R_4$ is methyl.

The most preferable compounds of our invention are the compounds defined according to the structure:

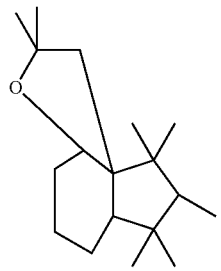

(3,3,10,10,11,12,12-heptamethyl-4-oxatricyclo[7.3.0.0<1,5>]dodecane; also named decahydro-2,2,4,4,5,6,6-heptamethyl-indeno[4,3A-B]furan) isomers of which have, for example, the structures:

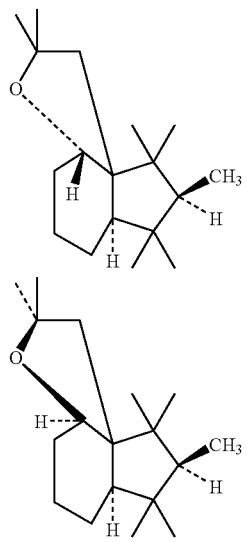

Such isomers, taken alone or in admixture, are useful in formulating fragrance compositions in accordance with the practice of our invention. More specifically, such isomers are set forth in the following Table I:

TABLE I

| | |
|---|---|
| (1R,5R,9R,11R)-Z | (1R,5S,9R,11S)-Z |
| (1R,5R,9R,11S)-Z | (1R,5R,9S,11S)-Z |
| (1R,5R,9S,11R)-Z; | (1R,5S,9S,11R)-Z |
| (1R,5S,9R,11R)-Z; | (1R,5S,9S,11S)-Z |
| (1S,5R,9R,11R)-Z; | (1S,5R,9S,11S)-Z |
| (1S,5R,9R,11S)-Z; | (1S,5S,9R,11S)-Z |
| (1S,5R,9S,11R)-Z; | (1S,5S,9S,11R)-Z |
| (1S,5S,9R,11R)-Z; | (1S,5S,9S,11S)-Z | wherein "Z" represents the compound name, "3,3,10,10,11,12,12-heptamethyl-4-oxatricyclo[7.3.0.0<1,5>]dodecane".

Thus, those with skill in the art will recognize that the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as HPLC, and particularly gel chromatography and solid phase microextraction ("SPME").

The compounds defined according to the structure:

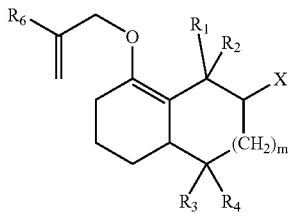

are prepared by means of an exchange reaction of allyl alcohol or methallyl alcohol with the corresponding $C_1$-$C_3$ alkyl enol ether in the presence of a catalytic amount of a protonic acid, preferably para-toluene sulfonic acid or methane sulfonic acid at a temperature in the range of 85° C. to about 105° C. according to the reaction:

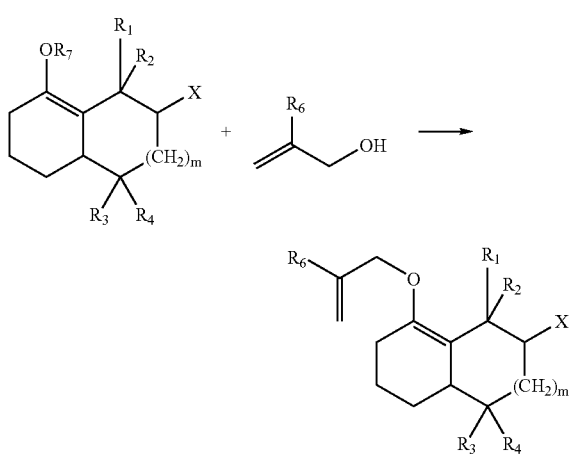

The resulting allyl or methallyl enol ethers may be recovered and used for their organoleptic properties, or each of them may be rearranged via a Claisen rearrangement at about 190-210° C. in the presence of a mild acid catalyst such as phosphoric acid, potassium diacid phosphate, sodium diacid phosphate, sodium bisulfate, the acid ion exchange catalyst, AMBERLYST 15 (trademark of the Rohm and Haas Company of Philadelphia, Pa., U.S.A.), disodium citrate, or hydroquinone according to the reaction:

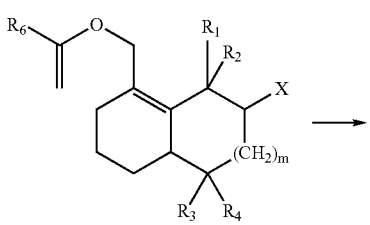

-continued

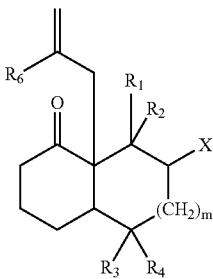

The resulting 3A-allyl or 3A-methallyl-4-ketone derivatives may be isolated and used for their respective organoleptic properties, or they may be subjected to carbonyl moiety-reduction using a metal hydride reducing agent, for example $LiAlH_4$ or sodium bis(2-methoxyethoxy)aluminum hydride (VITRIDE) to form the corresponding 3A-allyl or 3A-methallyl-4-hydroxy derivative according to the reaction:

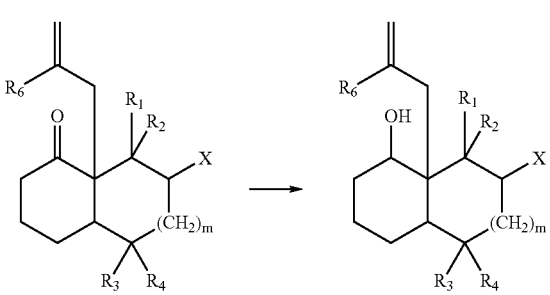

The resulting 3A-allyl or 3A-methallyl-4-hydroxy derivative may be recovered and used for its organoleptic properties or it may be cyclized with a protonic acid cyclizing reagent, preferably methane sulfonic acid in nitropropane at 18-40° C., according to the reaction:

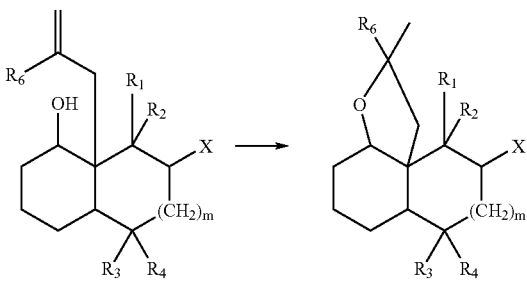

The compounds having the structure:

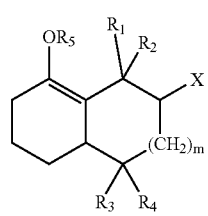

are prepared either according to the reaction:

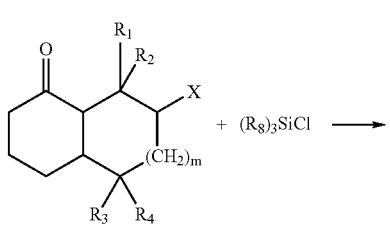

where $R_5$ is trialkyl silyl, or according to the reaction:

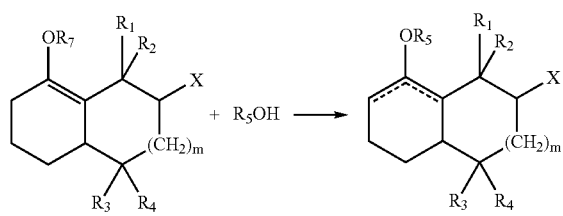

where $R_5$ is $C_4$-$C_7$ cycloalkyl or $C_4$-$C_7$ hydroxyalkenyl and where the dashed lines are indicative of mixtures of double bond position isomers wherein in such mixtures, one of the dashed lines represents a carbon-carbon double bond and the other of the dashed lines represents a carbon-carbon single bond. In both cases, the Δ3A,4 and Δ4,5 double bond position isomers are produced in admixture, and may, if desired, be separated prior to use for their respective organoleptic properties, according to techniques well known to those having ordinary skill in the art.

The compounds having the structure:

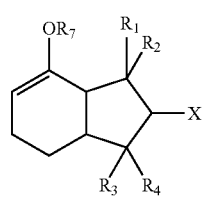

are prepared according to one of the following reactions:

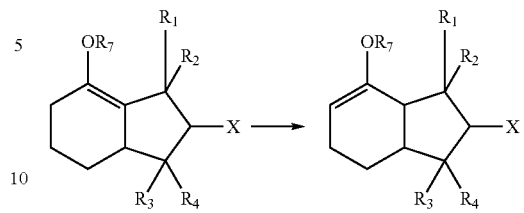

taking place in the presence of γ-alumina, or

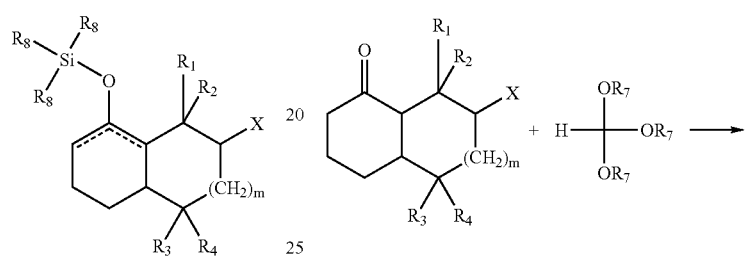

wherein a mixture of double-bond position isomers is formed, wherein one of the dashed lines is a carbon-carbon double bond and the other of the dashed lines is a carbon-carbon single bond, or

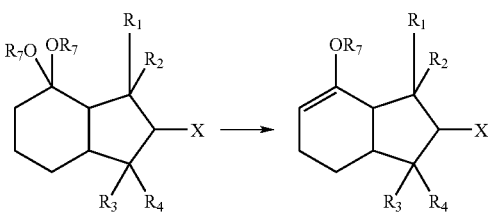

taking place at a temperature in the range of from about 125 to about 150° C. in the presence of γ-alumina and an inert solvent having a boiling point at atmospheric pressure of greater than 160° C., preferably toluene or p-dimethyl benzene. Most preferably, $R_7$ is methyl.

The latter two reactions each effect the formation of the mixture of the Δ3A,4 and Δ4,5 double bond position isomers which may, if desired, be separated using techniques well known to those having ordinary skill in the art.

The compounds and mixtures of compounds of the present invention have powerful and substantive woody, cigar box, amber aromas, with sweet musky, amber, creamy topnotes and strong floral, cedar, balsamic, sweet musky, amber and woody undertones.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; and musk and flower scents such as lavender-like, rose-like, iris-like, and carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the fragranced article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers and polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to mean parts per million; mm is understood to be millimeters, ml is understood to be milliliters, Bp is understood to be boiling point, THF is understood to be tetrahydrofuran, Hg is understood to be mercury and g is understood to be grams. IFF as used in the examples is understood to mean International Flavors & Fragrances Inc., New York, N.Y., USA.

EXAMPLE I

Preparation of 1,1,2,3,3-pentamethyl-7-(2-methyl-prop-2-enyloxy)-2,3,4,5,6,3A-hexahydroindene Reaction:

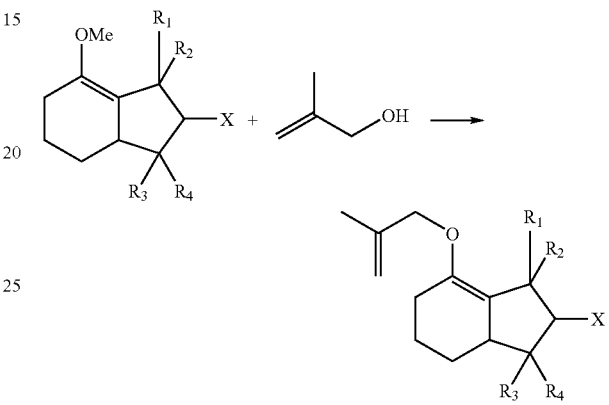

Into a 5 liter reaction vessel equipped with a thermocouple, 12" Goodloe packed column attached with take-off rushover still, mechanical stirrer, nitrogen line and addition funnel were placed 507 g (2 moles) of 1,1,2,3,3-pentamethyl-7-(2-methoxy)-2,3,4,5,6,3A-hexahydroindene prepared according to the procedure of Example I of U.S. Pat. No. 5,665,698, 288 g (4 moles) of methallyl alcohol and 1.1 g of p-toluene sulfonic acid.

The resulting reaction mixture, with stirring, was heated to 85° C. and maintained at that temperature for a period of 5 hours, while taking off the methanol reaction product.

The resulting reaction mixture was then quenched by adding 1.5 g of a 30% sodium methoxide solution and then romoving lights via vacuum evaporation. The resulting product was then transferred to a rushover distillation apparatus and distilled at 1.8-2.0 mm Hg. The crude material was distilled in an 18" Goodloe Column at a vapor temperature range of 129-131° C. and a pressure of 3.01-3.25 mm Hg.

The nmr spectrum of the product having the structure:

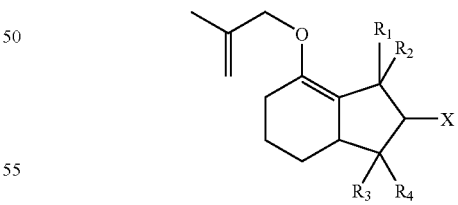

(a mixture wherein in the major compound (90%) X, $R_1$, $R_2$, $R_3$ and $R_4$ each is methyl and in the minor compounds X is hydrogen and one of $R_1$, $R_2$, $R_3$ and $R_4$ is ethyl and each of the other of $R_1$, $R_2$, $R_3$ and $R_4$ is methyl) is as follows:

0.68-1.1 ppm (ms, 15H); 1.25-2.2 ppm (m, 7H); 1.75 ppm (s, 3H); 4.1 ppm (d, 2H);

4.85-5.1 ppm (2s, 2H)

The product had an intense and substantive woody, cigar box aroma with cedar undertones.

EXAMPLE II

Preparation of Octahydro-1,1,2,3,3-pentamethyl-3A-(2-methyl-2-propenyl)-4H-inden-4-one Reaction:

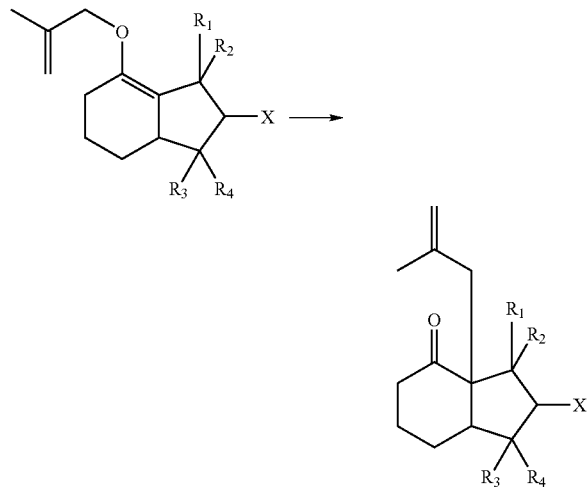

Into a 5 liter reaction flask equipped with a thermocouple, condenser, mechanical stirrer, nitrogen line and fluid metering pump for addition was placed 50 g Primol (Mineral Oil) and 1 g $NaH_2PO_4$.

With stirring, the resulting mixture was heated to 190-195° C. Using the metering pump, over a period of 1.5 hours while maintaining the reaction mixture temperature at 190-210° C., 538 g (1.72 moles) of the product of Example I, containing 90% 1,1,2,3,3-pentamethyl-7-(2-methylprop-2-enyloxy)-2,3,4,5,6,3A-hexahydroindene was added to the reaction mixture.

The reaction mixture was then transferred into a rushover distillation apparatus and the crude material was distilled at 1.0-2.0 mm Hg. The product was then transferred to an 18" Goodloe column and fractionally distilled at 165° C. and 1.8 mm Hg.

The nmr spectrum of the resulting product having the structure:

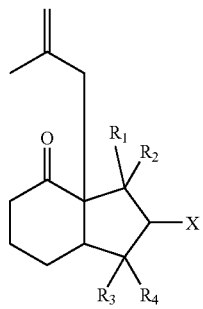

(a mixture wherein in the major compound (90%) X, $R_1$, $R_2$, $R_3$ and $R_4$ each is methyl and in the minor compounds X is hydrogen and one of $R_1$, $R_2$, $R_3$ and $R_4$ is ethyl and each of the other of $R_1$, $R_2$, $R_3$ and $R_4$ is methyl) is as follows:

0.76-1.13 ppm (ms, 15H); 1.57 ppm (s, 3H); 1.7 ppm (m, 2H); 1.85 ppm (m, 2H);
1.95-2.86 ppm (m, 7H); 4.68-4.86 ppm (2s, 2H).

The product had a woody aroma with intense, amber topnotes.

EXAMPLE II

Preparation of Octahydro-1,1,2,3,3-pentamethyl-3A-(2-methyl-2-propenyl)-4H-inden-4-ol Reaction:

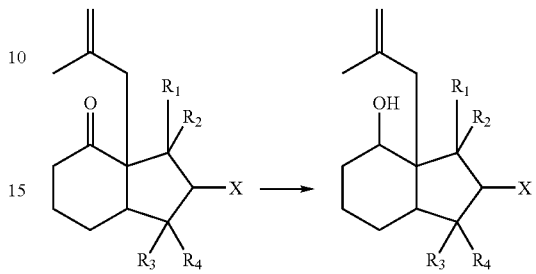

Into a 5 liter reaction flask equipped with a thermocouple, mechanical stirrer, nitrogen line and addition funnel was placed 718 g (2.74 moles) of the octahydro-1,1,2,3,3-pentamethyl-3A-(2-methyl-2-propenyl)-4H-inden-4-one prepared according to Example II.

550 Grams $LiAlH_4$ in 250 ml tetrahydrofuran was slowly added, while carefully cooling the reaction mass, causing the reaction temperature to rise to a maximum of 70° C.

The reaction mass was maintained, with stirring, at 70° C. for a period of 0.5 hours.

At the end of the 0.5 hour period, the reaction mass was quenched initially with ethyl acetate (in order to decompose the excess $LiAlH_4$) followed by addition of 1000 ml. aqueous 3M NaOH.

The reaction mass resulted in two phases: an aqueous phase and an organic phase. The aqueous layer was separated and the organic layer was further washed with two 1000 ml. portions of concentrated aqueous NaCl, dried over anhydrous $Na_2SO_4$ and filtered through CELITE (World Minerals Inc.)

The organic layer was then transferred to a rushover distillation apparatus where 470 g solvent was initially removed, followed by distillation to yield crude product over a temperature range of 107-151° C. and a pressure range of 5-9 mm. Hg. The product was then distilled on a 18"×1.5" Goodloe column at 175° C. and 6.5 mm Hg pressure.

The nmr spectrum of the resulting product having the structure:

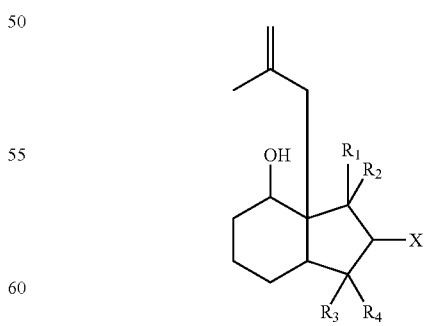

(a mixture wherein in the major compound (90%) X, $R_1$, $R_2$, $R_3$ and $R_4$ each is methyl and in the minor compounds X is hydrogen and one of $R_1$, $R_2$, $R_3$ and $R_4$ is ethyl and each of the other of $R_1$, $R_2$, $R_3$ and $R_4$ is methyl) is as follows:

1.25-1.78 ppm (m, 9H); 0.7-1.1 ppm (ms, 15H); 1.86 ppm (s, 3H); 2.05-2.65 ppm (m, 4H);
4.8-4.95 ppm (2s, 2H).

The product had a woody aroma with intense, amber topnotes.

EXAMPLE IV

Preparation of Decahydro-2,2,4,4,5,6,6-heptamethyl-indeno[4,3A-B]furan

Reaction:

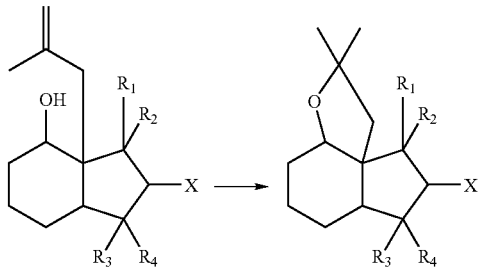

Into a 5 liter reaction flask equipped with a thermocouple, mechanical stirrer, nitrogen line, addition funnel and rushover distillation column was placed 300 g 1-nitropropane and 452 g (1.17 moles) of the octahydro-1,1,2,3,3-pentamethyl-3A-(2-methyl-2-propenyl)-4H-inden-4-ol prepared according to Example III.

10 ml. of methanesulfonic acid was slowly added to the resulting mixture, with stirring, causing the temperature of the mixture to rise to 30° C. The reaction mass was then stirred for a period of 0.5 hours. An additional 5 ml. of methanesulfonic acid was then added, with stirring, to the reaction mixture while maintaining the temperature at 30° C. The reaction mass was then stirred for a period of 0.5 hours. An additional 15 ml. of methanesulfonic acid was then added, with stirring, to the reaction mixture while maintaining the temperature at 30° C. The reaction mass was then stirred for a period of 0.5 hours. The reaction mass was then stirred for an additional 4 hours while maintaining the temperature at 30° C.

After the four hour period, the reaction mass was quenched with 250 ml. of $Na_2CO_3$ and stirred for a period of 15 minutes. At this point in time, the pH of the reaction mass was in the range of 9-9.5. 250 ml. Water was then added, with stirring, to the reaction mass and stirring was continued for another 0.5 hours.

The reaction mass resulted in two phases: an aqueous phase and an organic phase. The organic layer was transferred to a rushover distillation apparatus where 470 g solvent was initially removed followed by unreacted octahydro-1,1,2,3,3-pentamethyl-3A-(2-methyl-2-propenyl)-4H-inden-4-ol at 175° C. at 6.5 mm Hg.

The crude rushed-over material was then fractionally distilled through a 18"×1.5" Goodloe column at a reflux ratio of 3:1 yielding 17 fractions. Fractions 6-16 distilling at 91° C. at 6.5 mm Hg pressure were bulked.

The nmr spectrum of the resulting product having the structure:

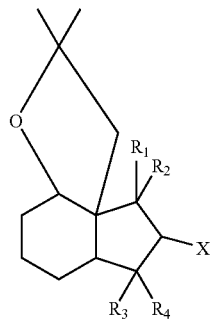

(a mixture wherein in the major compound (90%) X, $R_1$, $R_2$, $R_3$ and $R_4$ each is methyl and in the minor compounds X is hydrogen and one of $R_1$, $R_2$, $R_3$ and $R_4$ is ethyl and each of the other of $R_1$, $R_2$, $R_3$ and $R_4$ is methyl) is as follows:
0.65-1.07 ppm (ms, 15H); 1.3 ppm (s, 3H); 1.4 ppm (s, 3H); 1.55-2.46 ppm (m, 7H).

The product had an intense and substantive woody amber aroma with sweet musky topnotes and balsamic undertones.

EXAMPLE V

Preparation of 1,1,2,3,3-pentamethyl-7-(prop-2-enyloxy)-2,3,4,5,6,3A-hexahydroindene Reaction:

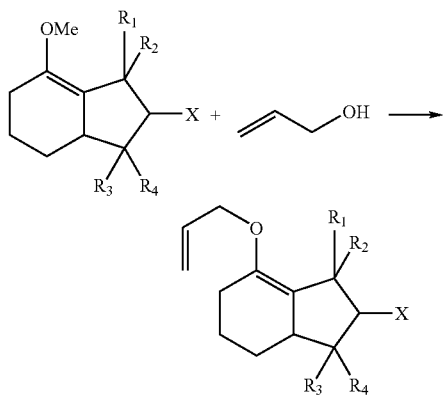

Into a 5 liter reaction vessel equipped with a thermocouple, 12" Goodloe packed column attached with take-off rushover still, mechanical stirrer, nitrogen line and addition funnel were placed 507 g (2 moles) of 1,1,2,3,3-pentamethyl-7-(2-methoxy)-2,3,4,5,6,3A-hexahydroindene prepared according to the procedure of Example I of U.S. Pat. No. 5,665,698, 240 g (4 moles) of allyl alcohol and 1.1 g of p-toluene sulfonic acid.

The resulting reaction mixture, with stirring, was heated to 85° C. and maintained at that temperature for a period of 5 hours, while taking off the methanol reaction product.

The resulting reaction mixture was then quenched by adding 1.5 g of a 30% sodium methoxide solution and then romoving lights via vacuum evaporation. The resulting product was then transferred to a rushover distillation apparatus and distilled, yielding the compounds having the structure:

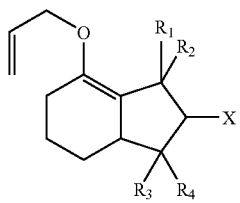

(a mixture wherein in the major compound (90%) X, $R_1$, $R_2$, $R_3$ and $R_4$ each is methyl and in the minor compounds X is hydrogen and one of $R_1$, $R_2$, $R_3$ and $R_4$ is ethyl and each of the other of $R_1$, $R_2$, $R_3$ and $R_4$ is methyl).

The product had a mahogany aroma with sweet, musky undertones.

EXAMPLE VI

Preparation of Octahydro-1,1,2,3,3-pentamethyl-3A-(2-propenyl)-4H-inden-4-one

Reaction:

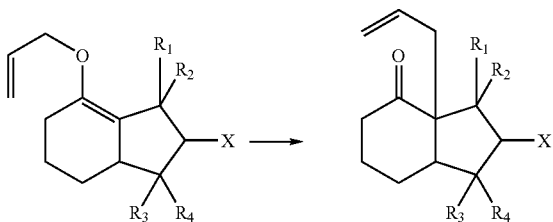

Into a 5 liter reaction flask equipped with a thermocouple, condenser, mechanical stirrer, nitrogen line and fluid metering pump for addition was placed 50 g Primol (Mineral Oil) and 5 g $KH_2PO_4$.

With stirring, the resulting mixture was heated to 190-195° C. Using the metering pump, over a period of 1.5 hours while maintaining the reaction mixture temperature at 190-210° C., 312 g of the product of Example V, containing 90% 1,1,2,3,3-pentamethyl-7-(prop-2-enyloxy)-2,3,4,5,6,3A-hexahydroindene was added to the reaction mixture.

The reaction mixture was then transferred into a rushover distillation apparatus and the crude material was distilled.

The product had an intense woody aroma with amber undertones.

The nmr spectrum of the resulting product having the structure:

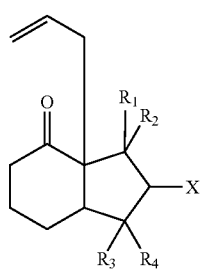

(a mixture wherein in the major compound (90%) X, $R_1$, $R_2$, $R_3$ and $R_4$ each is methyl and in the minor compounds X is hydrogen and one of $R_1$, $R_2$, $R_3$ and $R_4$ is ethyl and each of the other of $R_1$, $R_2$, $R_3$ and $R_4$ is methyl) is as follows:

0.73-1.06 ppm (ms, 15H); 1.2-2.4 ppm (m, 8H); 5.1 ppm (m, 2H); 5.5 ppm (m, 1H).

EXAMPLE VII

Preparation of Octahydro-1,1,2,3,3-pentamethyl-3A-(2-propenyl)-4H-inden-4-ol

Reaction:

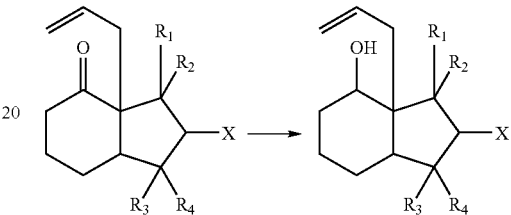

Into a 5 liter reaction flask equipped with a thermocouple, mechanical stirrer, nitrogen line and addition funnel was placed 656 g (1.77 moles) of the octahydro-1,1,2,3,3-pentamethyl-3A-(2-propenyl)-4H-inden-4-one prepared according to Example VI.

21.7 Grams $LiAlH_4$ in 260 ml tetrahydrofuran was slowly added, while carefully cooling the reaction mass, causing the reaction temperature to rise to a maximum of 70° C.

The reaction mass was maintained, with stirring, at 70° C. for a period of 0.5 hours.

At the end of the 0.5 hour period, the reaction mass was quenched initially with 20% aqueous acetic acid (in order to decompose the excess $LiAlH_4$) followed by addition of 1000 ml. aqueous 20% $NaHCO_3$.

The reaction mass resulted in two phases: an aqueous phase and an organic phase. The aqueous layer was separated and the organic layer is further washed with two 1000 ml. portions of concentrated aqueous NaCl, dried over anhydrous $Na_2SO_4$ and filtered through CELITE.

The organic layer was then transferred to a rushover distillation apparatus where 470 g solvent was initially removed, followed by distillation to yield crude product. The product was then distilled on a 18"×1.5" Goodloe column.

The product had an intense and substantive woody, amber aroma.

The nmr spectrum of the resulting product having the structure:

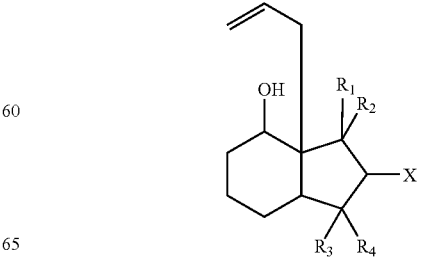

(a mixture wherein in the major compound (90%) X, $R_1$, $R_2$, $R_3$ and $R_4$ each is methyl and in the minor compounds X is hydrogen and one of $R_1$, $R_2$, $R_3$ and $R_4$ is ethyl and each of the other of $R_1$, $R_2$, $R_3$ and $R_4$ is methyl) is as follows:

0.7-1.1 ppm (ms, 15H); 1.35-1.8 ppm (m, 7H); 2.25-2.6 ppm (m, 2H); 3.95 ppm (m, 1H);

5.15 ppm (m, 2H); 6 ppm (m, 1H).

The infra-red spectrum is as follows:

3431 cm$^{-1}$ (—OH); 3074, 2958 cm$^{-1}$ (—C$\underline{H}$); 909 cm$^{-1}$ (>=CH$_2$).

EXAMPLE VIII

Preparation of Decahydro-2,4,4,5,6,6-hexamethyl-indeno[4,3A-B]furan

Reaction:

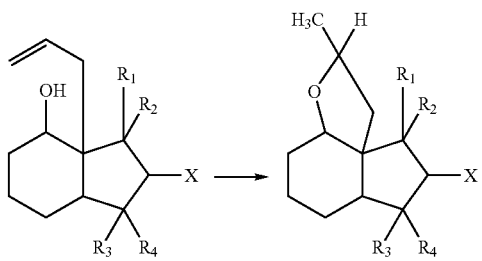

Into a 5 liter reaction flask equipped with a thermocouple, mechanical stirrer, nitrogen line, addition funnel and rush-over distillation column was placed 300 g 1-nitropropane and 452 g of the octahydro-1,1,2,3,3-pentamethyl-3A-(2-propenyl)-4H-inden-4-ol prepared according to Example VII.

10 ml. of methanesulfonic acid was slowly added to the resulting mixture, with stirring, causing the temperature of the mixture to rise to 30° C. The reaction mass was then stirred for a period of 0.5 hours. An additional 5 ml. of methanesulfonic acid was then added, with stirring, to the reaction mixture while maintaining the temperature at 30° C. The reaction mass was then stirred for a period of 0.5 hours. An additional 15 ml. of methanesulfonic acid was then added, with stirring, to the reaction mixture while maintaining the temperature at 30° C. The reaction mass was then stirred for a period of 0.5 hours. The reaction mass was then stirred for an additional 4 hours while maintaining the temperature at 30° C.

After the four hour period, the reaction mass was quenched with 250 ml. of Na$_2$CO$_3$ and stirred for a period of 15 minutes. At this point in time, the pH of the reaction mass was in the range of 9-9.5. 250 ml. Water was then added, with stirring, to the reaction mass and stirring was continued for another 0.5 hours.

The reaction mass resulted in two phases: an aqueous phase and an organic phase. The organic layer was transferred to a rushover distillation apparatus where the solvent was initially removed. The product was then transferred to an 18"×1.5" Goodloe distillation column and fractionally distilled yielding a product having an intense and substantive woody, amber aroma with sweet, musky topnotes and balsamic undertones and compounds having the following structure:

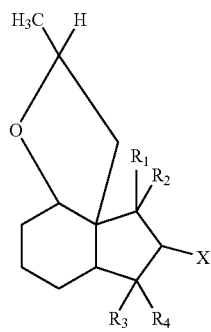

(a mixture wherein in the major compound (90%) X, $R_1$, $R_2$, $R_3$ and $R_4$ each is methyl and in the minor compounds X is hydrogen and one of $R_1$, $R_2$, $R_3$ and $R_4$ is ethyl and each of the other of $R_1$, $R_2$, $R_3$ and $R_4$ is methyl).

EXAMPLE IX

Preparation of 4-[(2,3,5,6,7,7A-hexahydro-1,1,2,3,3-pentamethyl-1H-inden-4-yl)oxy]-2Z-buten-1-ol Reaction:

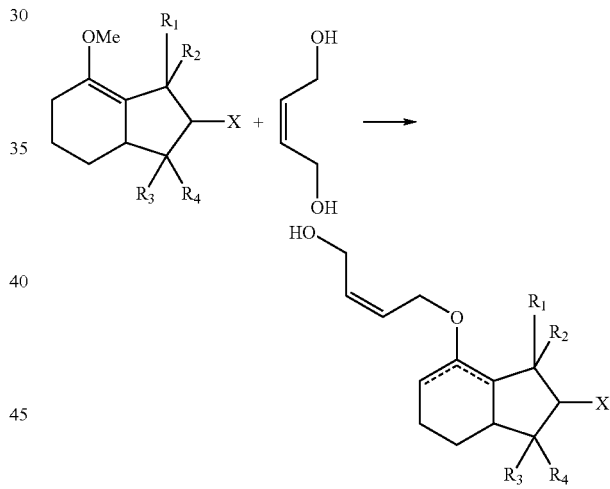

(wherein the dashed lines indicate a mixture of double bond position isomers wherein in each of the compounds of the mixture one of the dashed lines is a carbon-carbon double bond and the other of the dashed lines is a carbon-carbon single bond)

Into a 5 liter reaction vessel equipped with a thermocouple, 12" Goodloe packed column attached with take-off rushover still, mechanical stirrer, nitrogen line and addition funnel were placed 507 g (2 moles) of 1,1,2,3,3-pentamethyl-7-(2-methoxy)-2,3,4,5,6,3A-hexahydroindene prepared according to the procedure of Example I of U.S. Pat. No. 5,665,698, 240 g of 1,4-dihydroxy-2Z-butene and 1.1 g of p-toluene sulfonic acid.

The resulting reaction mixture, with stirring, was heated to 85° C. and maintained at that temperature for a period of 5 hours, while taking off the methanol reaction product.

The resulting reaction mixture was then quenched by adding 1.5 g of a 30% sodium methoxide solution and then romoving lights via vacuum evaporation. The resulting product was then transferred to a rushover distillation apparatus and distilled, yielding the compounds having the following structure and the following nmr spectrum:

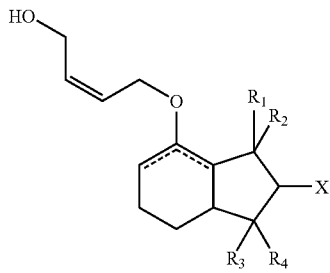

(a mixture wherein in the major compound (90%) X, $R_1$, $R_2$, $R_3$ and $R_4$ each is methyl and in the minor compounds X is hydrogen and one of $R_1$, $R_2$, $R_3$ and $R_4$ is ethyl and each of the other of $R_1$, $R_2$, $R_3$ and $R_4$ is methyl).

0.64-1.09 ppm (ms, 15H); 1.61-2.12 ppm (m, 7H); 2.88 ppm (s, 1H); 4 ppm (m, 2H);

4.37 ppm (m, 2H); 5.66 ppm (m, 1H); 5.80 ppm (m, 1H).

The product had a woody, sweet musky aroma with floral undertones.

EXAMPLE X

Preparation of 7-(cyclohexyloxy)-2,3,3A,4,5,6-hexahydro-1,1,2,3,3-pentamethyl-1H-indene Reaction:

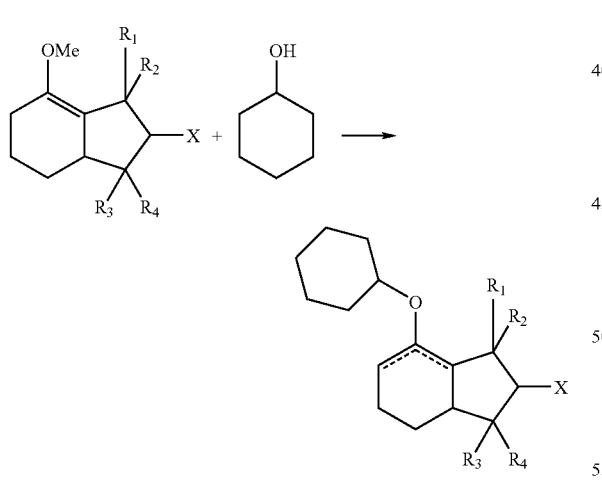

(wherein the dashed lines indicate a mixture of double bond position isomers wherein in each of the compounds of the mixture one of the dashed lines is a carbon-carbon double bond and the other of the dashed lines is a carbon-carbon single bond).

Into a 5 liter reaction vessel equipped with a thermocouple, 12" Goodloe packed column attached with take-off rushover still, mechanical stirrer, nitrogen line and addition funnel were placed 109 g of 1,1,2,3,3-pentamethyl-7-(2-methoxy)-2,3,4,5,6,3A-hexahydroindene prepared according to the procedure of Example I of U.S. Pat. No. 5,665,698, 100 g of cyclohexanol and 0.34 g of p-toluene sulfonic acid.

The resulting reaction mixture, with stirring, was heated to 90° C. and maintained at that temperature for a period of 2.5 hours, while taking off the methanol reaction product.

The resulting reaction mixture was then quenched by adding 1.5 g of a 30% sodium methoxide solution and then romoving lights via vacuum evaporation. The resulting product was then transferred to a rushover distillation apparatus and distilled, yielding the compounds which possess a woody, sweet musky aroma with amber topnotes, and having the following structure (a 2:1 mixture of Δ7,7A and Δ6,7 double-bond position isomeric compounds) and the following nmr spectrum:

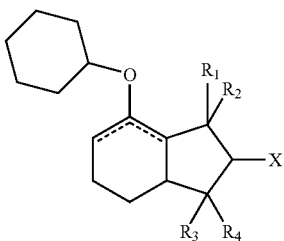

(a mixture wherein in the major compound (90%) X, $R_1$, $R_2$, $R_3$ and $R_4$ each is methyl and in the minor compounds X is hydrogen and one of $R_1$, $R_2$, $R_3$ and $R_4$ is ethyl and each of the other of $R_1$, $R_2$, $R_3$ and $R_4$ is methyl).

0.68-0.95 ppm (ms, 15H); 1.1-2.3 ppm (m, 17H); 3.8 ppm (m, 1H); 5.25 ppm (m, 1H).

EXAMPLE XI

Preparation of [(2,3,5,6,7,7A-hexahydro-1,1,2,3,3-pentamethyl-1H-inden-4-yl)oxy]trimethyl-silane Reaction:

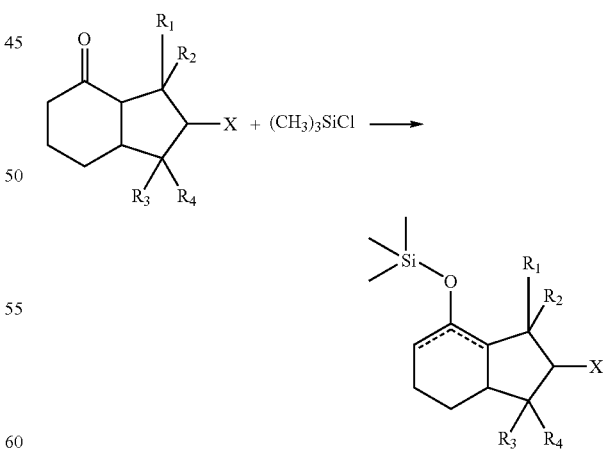

(wherein the dashed lines indicate a mixture of double bond position isomers wherein in each of the compounds of the mixture one of the dashed lines is a carbon-carbon double bond and the other of the dashed lines is a carbon-carbon single bond).

Into a 5 liter reactor equipped with stirrer, thermometer, heating mantle, nitrogen tube, addition funnel and reflux condenser were placed dimethyl formamide, triethyl amine and trimethyl silyl chloride. The resulting mixture was heated, with stirring, to 70° C. under a nitrogen atmosphere. Over a period of 0.25 hours, with stirring, dihydrocashmeran, having the structure:

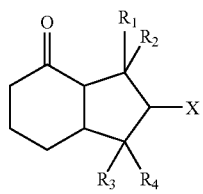

was added to the reaction mass. The reaction mass was heated to 80° C. and maintained at 80° C. for a period of 10 hours. The reaction mass was cooled to ambient temperature and 200 gm toluene was then added, with stirring. The reaction mass was then quenched with 400 ml. water and the resulting organic phase was then washed with one 200 ml. volume of water. The resulting product was distilled at 120° C. and 3 mm Hg pressure yielding compounds with the following structure and nmr spectrum:

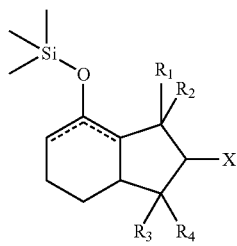

(a mixture wherein in the major compound (90%) X, $R_1$, $R_2$, $R_3$ and $R_4$ each is methyl and in the minor compounds X is hydrogen and one of $R_1$, $R_2$, $R_3$ and $R_4$ is ethyl and each of the other of $R_1$, $R_2$, $R_3$ and $R_4$ is methyl).

0.18 ppm (s, 9H); 0.58-1.1 ppm (ms, 15H); 1.38-2.2 ppm (m, 7H).

The product had a woody, floral aroma with soft woody, creamy topnotes.

EXAMPLE XII

Preparation of 2,3,3A,4,5,7A-hexahydro-7-methoxy-1,1,2,3,3-pentamthyl-1H-indene

Reaction:

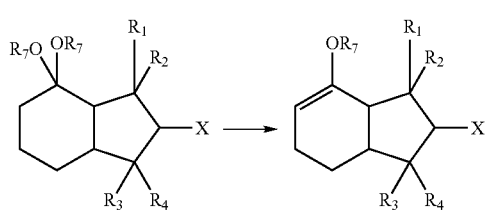

(wherein $R_7$ is methyl).

Into a 5 liter reactor equipped with thermometer, reflux condenser, dean-stark trap, stirrer and heating mantle were placed 10 g γ-alumina (alumina activated for 0.25 hours at 200° C.), 100 g toluene and 200 g 1,1,2,3,3-pentamethyl-4,4-dimethoxyindane prepared according to the procedure of U.S. Pat. No. 5,665,698. With stirring, the resulting mixture was heated to reflux and refluxed for a period of 9 hours, while collecting reaction product in a dean-stark trap. The resulting product, prior to distillation was a 6:1 mixture of Δ4,5 and Δ3A,4 double-bond isomers.

The structure of the major product and the nmr spectrum of the product are as follows:

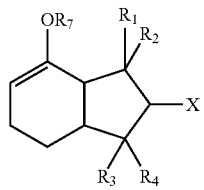

wherein $R_7$ is methyl and wherein the resulting product is a mixture wherein in the major compound (90%) X, $R_1$, $R_2$, $R_3$ and $R_4$ each is methyl and in the minor compounds X is hydrogen and one of $R_1$, $R_2$, $R_3$ and $R_4$ is ethyl and each of the other of $R_1$, $R_2$, $R_3$ and $R_4$ is methyl.

0.68-1.1 ppm (ms, 15H); 1.27-2.15 ppm (m, 7H); 3.45 ppm (s, 3H); 4.45 ppm (m, 1H).

The product had an intense and substantive woody, sweet musky aroma with balsamic undertones.

EXAMPLE XIII

Perfume Formulations

Fragrances were prepared according to the following formulations:

| Materials | Parts by weight | | |
|---|---|---|---|
| | Example XIII(a) | Example XIII(b) | Example XIII(c) |
| Decahydro-2,2,4,4,5,6,6-heptamethyl-indeno[4,3A-B]furan prepared according to Example IV | 0 | 0 | 4 |
| [(2,3,5,6,7,7A-hexahydro-1,1,2,3,3-pentamethyl-1H-inden-4-yl)oxy]trimethyl-silane prepared according to Example XI | 0 | 4 | 0 |
| Decahydro-2,4,4,5,6,6-hexamethyl-indeno[4,3A-B]furan prepared according to Example VIII | 4 | 0 | 0 |
| BORNAFIX ® (IFF) | 3 | 3 | 3 |
| CEDRAFIX ® (IFF) | 2.5 | 2.5 | 2.5 |
| CELESTOLIDE ® (IFF) | 4 | 4 | 4 |
| CITRALVA ® (IFF) | 1 | 1 | 1 |
| Citrus oil distilled | 12 | 12 | 12 |
| CYCLACET ® (IFF) | 3 | 3 | 3 |
| CYCLOGALBANIFF ® (IFF) | 1 | 1 | 1 |
| Dihydro Myrcenol | 40 | 40 | 40 |
| FLEURANIL ® (IFF) | 1 | 1 | 1 |
| Geranium Bourbon Oliffac | 0.5 | 0.5 | 0.5 |
| Hexyl Cinnamic Aldehyde | 4.5 | 4.5 | 4.5 |
| ISO E SUPER ® (IFF) | 2.5 | 2.5 | 2.5 |
| KHARISMAL ® (IFF) | 2 | 2 | 2 |
| KOAVONE ® (IFF) | 1.5 | 1.5 | 1.5 |

-continued

| Materials | Parts by weight | | |
|---|---|---|---|
| | Example XIII(a) | Example XIII(b) | Example XIII(c) |
| Linalyl Acetate | 5 | 5 | 5 |
| PHENOXANOL ® (IFF) | 3 | 3 | 3 |
| PRECYCLEMONE B ® (IFF) | 1.5 | 1.5 | 1.5 |
| Pseudo Linalyl Acetate | 5 | 5 | 5 |
| Styralyl Acetate | 1 | 1 | 1 |
| VIGOFLOR ® | 1 | 1 | 1 |
| ZENOLIDE ® (IFF) | 4 | 4 | 4 |

The indenofurans of Examples IV and VIII each impart to this citrus fragrance, intense and substantive woody, amber, and balsamic undertones and sweet musky topnotes. Accordingly, the fragrances of Examples XIII(a) and XIII(c) can be described has being a citrus fragrance with intense and substantive woody, amber, and balsamic undertones and sweet musky topnotes.

The indenyl silane of Example XI imparts to this citrus fragrance woody and floral undertones and soft woody, and creamy topnotes. Accordingly, the fragrance of Example XIII(B) can be described as being a citrus fragrance with woody and floral undertones and soft woody, and creamy topnotes.

EXAMPLE XIV

Preparation of Cosmetic Powder Compositions

Cosmetic powder compositions were prepared by mixing in a ball mill 100 grams of talcum powder with 0.25 grams of each of the substances set forth in Table II below. Each of the cosmetic powder compositions had an excellent aroma as described in Table II below.

TABLE II

| Substance | Aroma Description |
|---|---|
| 1,1,2,3,3-Pentamethyl-7-(2-methylprop-2-enyloxy)-2,3,4,5,6,3A-hexahydroindene prepared according to Example I | An intense and substantive woody, cigar box aroma with cedar undertones |
| Decahydro-2,2,4,4,5,6,6-heptamethyl-indeno[4,3A-B]furan prepared according to Example IV | An intense and substantive woody, amber aroma with sweet musky topnotes and balsamic undertones |
| [(2,3,5,6,7,7A-Hexahydro-1,1,2,3,3-pentamethyl-1H-inden-4-yl)oxy]trimethyl-silane prepared according to Example XI | A woody, floral aroma with soft woody, creamy topnotes |
| Decahydro-2,4,4,5,6,6-hexamethyl-indeno[4,3A-B]furan prepared according to Example VIII | An intense and substantive woody amber aroma with sweet, musky topnotes and balsamic undertones |
| 2,3,3A,4,5,7A-Hexahydro-7-methoxy-1,1,2,3,3-pentamthyl-1H-indene prepared according to Example XII | An intense and substantive woody, sweet, musky aroma with balsamic undertones |
| Perfume Composition of Example XIII(a) | A citrus aroma with intense and substantive woody, amber, and balsamic undertones and sweet musky topnotes |
| Perfume Composition of Example XIII(b) | A citrus aroma with woody and floral undertones and soft woody, and creamy topnotes |
| Perfume Composition of Example XIII(c) | A citrus aroma with intense and substantive woody, amber, and balsamic undertones and sweet musky topnotes |

EXAMPLE XV

Preparation of Soap Compositions 100 grams of soap chips (per sample) (IVORY® produced by the Procter & Gamble Company of Cincinnatti, Ohio, U.S.A.) were each mixed with 1 gram samples of substances as set forth in Table II of Example XIV until homogeneous compositions were obtained. In each of the cases, the homogeneous compositions were heated under 8.5 atmospheres pressure at 183° C. for a period of 3.5 hours and the resulting liquids were placed in soap molds. The resulting soap cakes, on cooling, provided aromas as set forth in Table II of Example XIV.

What is claimed is:

1. A compound defined according to the structure:

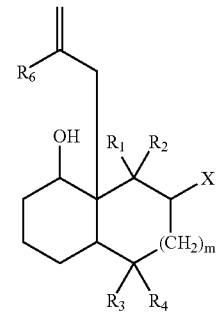

wherein is 0 or 1;
wherein X is methyl or hydrogen;
wherein $R_1$, $R_2$, $R_3$ and $R_4$ each represent methyl or ethyl with the proviso that when X is methyl, each of $R_1$, $R_2$, $R_3$ and $R_4$ is methyl and when X is hydrogen, one of $R_1$, $R_2$, $R_3$ and $R_4$ is ethyl; and
wherein $R_6$ hydrogen or methyl.

2. A compound defined according to the structure:

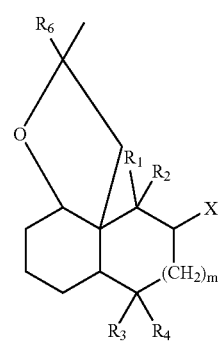

wherein m is 0 or 1;
wherein X is methyl or hydrogen;
wherein $R_1$, $R_2$, $R_3$ and $R_4$ each represent methyl or ethyl with the proviso that when X is methyl, each of $R_1$, $R_2$, $R_3$ and $R_4$ is methyl and when X is hydrogen, one of $R_1$, $R_2$, $R_3$ and $R_4$ is ethyl; and
wherein $R_6$ hydrogen or methyl.

3. A compound of claim 2 defined according to the structure:

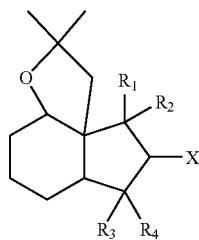

wherein X is methyl or hydrogen; and
wherein $R_1$, $R_2$, $R_3$ and $R_4$ each represent methyl or ethyl with the proviso that when X is methyl, each of $R_1$, $R_2$, $R_3$ and $R_4$ is methyl and when X is hydrogen, one of $R_1$, $R_2$, $R_3$ and $R_4$ is ethyl.

4. A compound defined according to the structure:

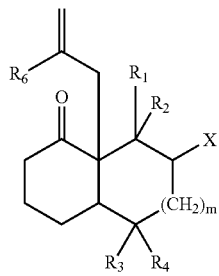

wherein m is 0 or 1;
wherein X is methyl or hydrogen;
wherein $R_1$, $R_2$, $R_3$ and $R_4$ each represent methyl or ethyl with the proviso that when X is methyl, each of $R_1$, $R_2$, $R_3$ and $R_4$ is methyl and when X is hydrogen, one of $R_1$, $R_2$, $R_3$ and $R_4$ is ethyl; and
wherein $R_6$ hydrogen or methyl.

5. A compound of claim 3 having the structure:

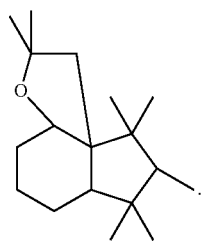

6. The optical isomers of the compound of claim 5:

| | |
|---|---|
| (1R,5R,9R,11R)-Z | (1R,5S,9R,11S)-Z |
| (1R,5R,9R,11S)-Z | (1R,5R,9S,11S)-Z |
| (1R,5R,9S,11R)-Z; | (1R,5S,9S,11R)-Z |
| (1R,5S,9R,11R)-Z; | (1R,5S,9S,11S)-Z |
| (1S,5R,9R,11R)-Z | (1S,5R,9S,11S)-Z |
| (1S,5R,9R,11S)-Z; | (1S,5S,9R,11S)-Z |
| (1S,5R,9S,11R)-Z; | (1S,5S,9S,11R)-Z |
| (1S,5S,9R,11R)-Z; | (1S,5S,9S,11S)-Z | wherein "Z" represents the compound name, "3,3,10,10,11,12,12-heptamethyl-4-oxatricyclo[7.3.0.0<1,5>]dodecane".

7. A method for improving, enhancing or modifying the odor properties of a fragrance by incorporating an olfactory acceptable amount of the compound of claim 2.

8. A method for improving, enhancing or modifying the odor properties of a fragrance by incorporating an olfactory acceptable amount of the compound of claim 3.

9. A method for improving, enhancing or modifying the odor properties of a fragrance by incorporating an olfactory acceptable amount of the compound of claim 5.

10. A method for improving, enhancing or modifying the odor properties of a fragrance by incorporating an olfactory acceptable amount of at least one isomer of claim 6.

11. A process for synthesizing the compound of claim 4 via the Claisen rearrangement reaction:

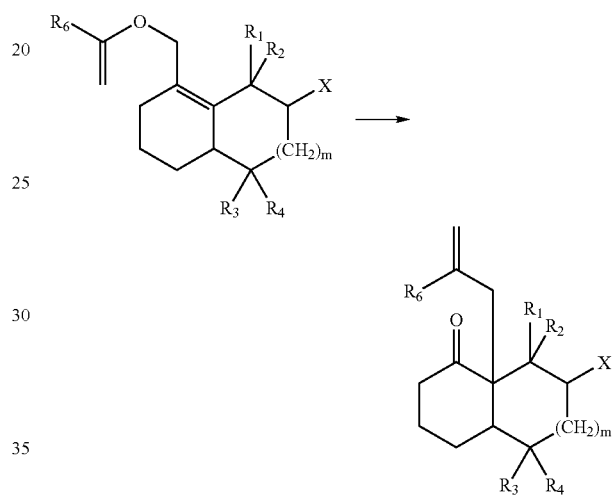

at about 190-210° C. in the presence of a mild acid catalyst, said catalyst is selected from the group consisting of phosphoric acid, potassium diacid phosphate, sodium diacid phosphate, sodium bisulfate, an acid ion exchange catalyst, disodium citrate and hydroquinone.

12. A process for preparing a compound defined according to claim 2 comprising the steps of first carrying out the reaction:

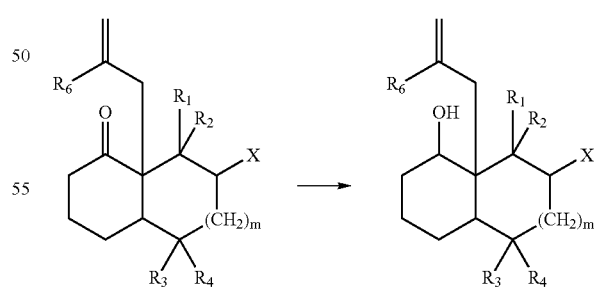

using a metal hydride reducing agent; and then carrying out the reaction:
using a protonic acid cyclizing agent.

* * * * *